United States Patent
Schweizer

(10) Patent No.: US 9,878,178 B2
(45) Date of Patent: Jan. 30, 2018

(54) METHOD AND MAGNETIC RESONANCE APPARATUS FOR QUALITY CONTROL IN PLANNING RADIOTHERAPY OF A PATIENT

(71) Applicant: Siemens Healthcare GmbH, Erlangen (DE)

(72) Inventor: Bernd Schweizer, Ketsch (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/215,740

(22) Filed: Jul. 21, 2016

(65) Prior Publication Data

US 2017/0021195 A1    Jan. 26, 2017

(30) Foreign Application Priority Data

Jul. 21, 2015   (DE) .................. 10 2015 213 730

(51) Int. Cl.
*A61N 5/10*      (2006.01)
*G01R 33/56*     (2006.01)
*G01R 33/48*     (2006.01)

(52) U.S. Cl.
CPC ....... *A61N 5/1039* (2013.01); *G01R 33/4808* (2013.01); *G01R 33/5608* (2013.01)

(58) Field of Classification Search
CPC ................................................. A61N 5/1039
See application file for complete search history.

(56) References Cited

U.S. PATENT DOCUMENTS

| | | |
|---|---|---|
| 2007/0263769 A1 | 11/2007 | Roell |
| 2016/0059041 A1 | 3/2016 | Grodzki et al. |
| 2016/0310761 A1* | 10/2016 | Li ................... A61N 5/1038 |
| 2017/0072222 A1* | 3/2017 | Siversson ........ A61N 5/1039 |
| 2017/0106210 A1* | 4/2017 | Grodzki .............. A61B 5/055 |

OTHER PUBLICATIONS

Korsholm et al.; "A Criterion for the Reliable Use of MRI-Only radio Therapy," Radiation Oncology, vol. 9, No. 16 (2014).
Roy. et al: PET attenuation correction using synthetic CT from ultrashort echo-time MRR imaging. J. Nucl. Med. vol. 55 pp. 2071-2077 (2014).
Zahra et al: "Semiquantitative and quantitative dynamic contrast-enhanced magnetic resonance imaging measurements predict radiation response in cervix cancer"; Int. J. Radiation Oncology Biol. Phys.; vol. 74 No. 3; pp. 766-773, (2009).

* cited by examiner

*Primary Examiner* — Glen Kao
(74) *Attorney, Agent, or Firm* — Schiff Hardin LLP

(57) ABSTRACT

In a quality control method and computer for planning radiotherapy of patient, magnetic resonance (MR) image data, acquired from a planning volume of a patient, are provided to a computer and are used in the computer to generate a first electron density map of the planning volume. A second electron density map is generated using the first electron density map, wherein a value of electron density for a bone region in the planning volume is reduced compared to the first electron density map. First and second radiation dose distributions in the planning volume are respectively determined from the radiotherapy plan and the first electron density map, and the radiotherapy plan and the second electron density map. These distributions are compared in order to generate output information.

15 Claims, 3 Drawing Sheets

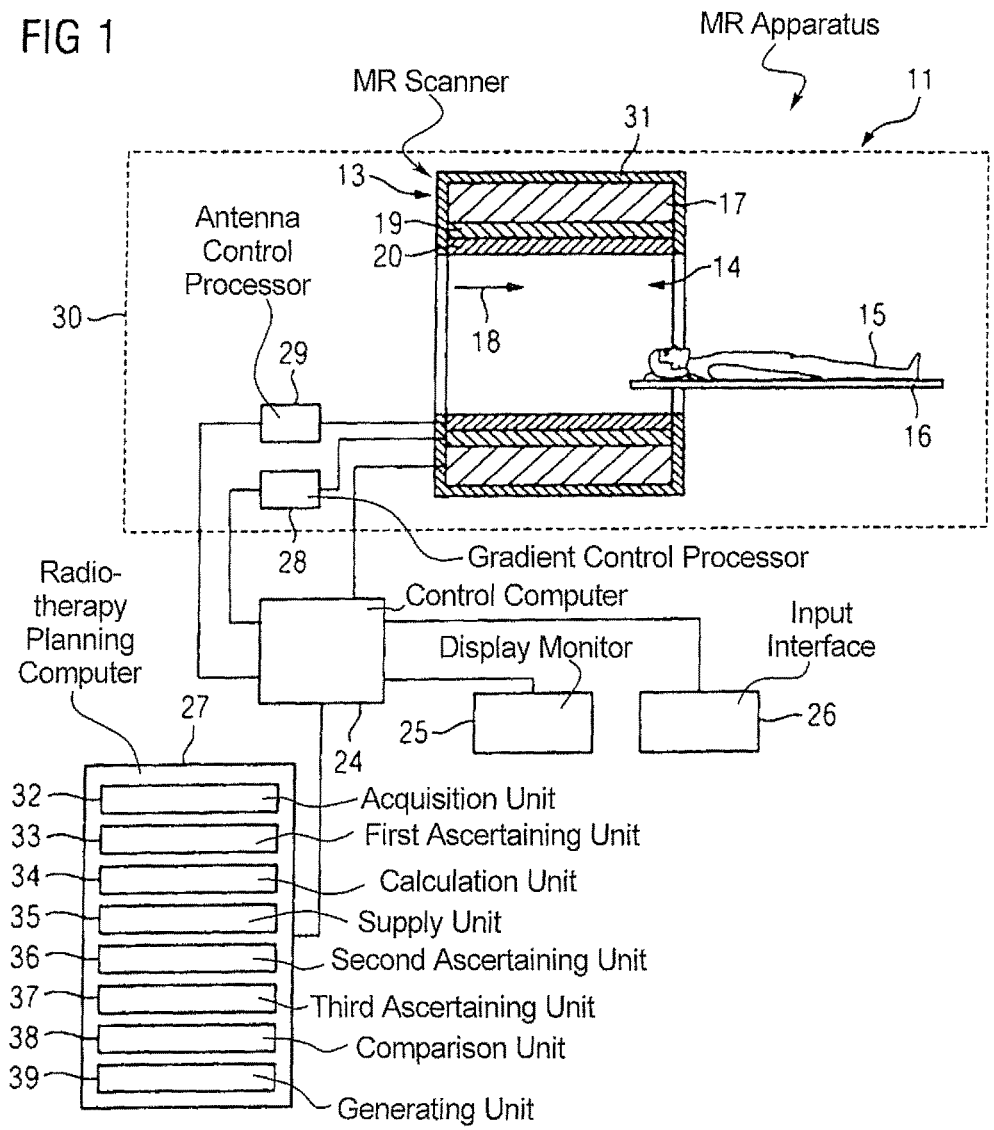

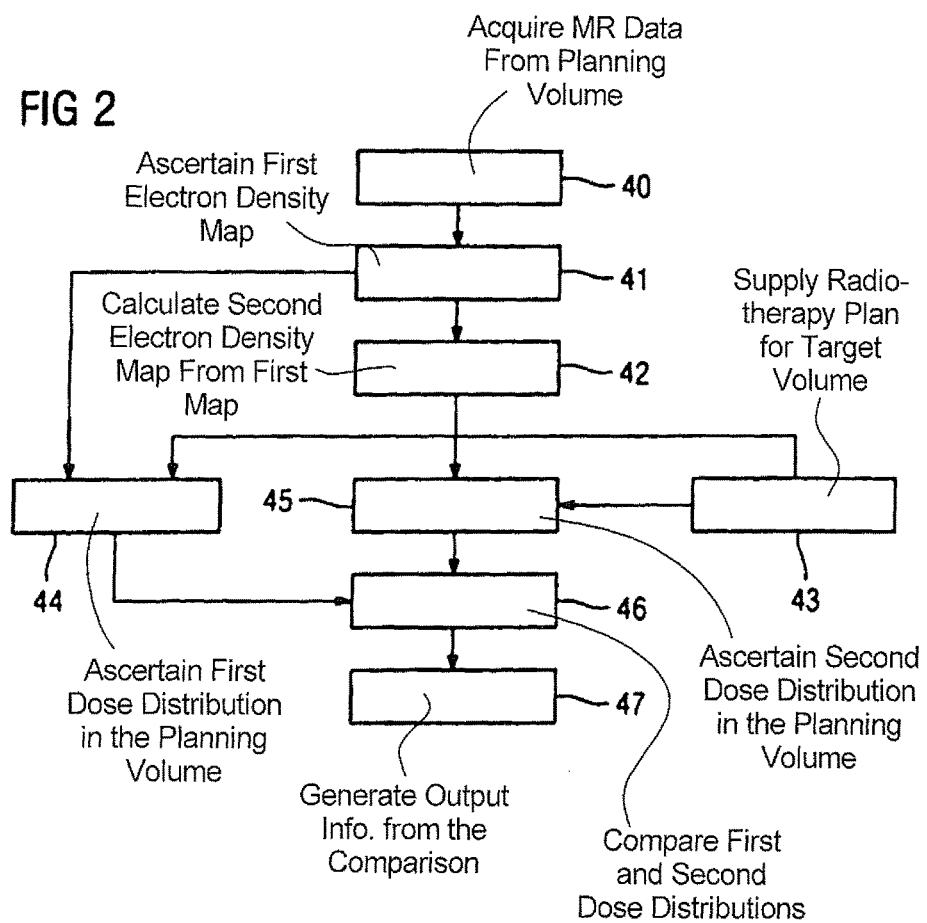

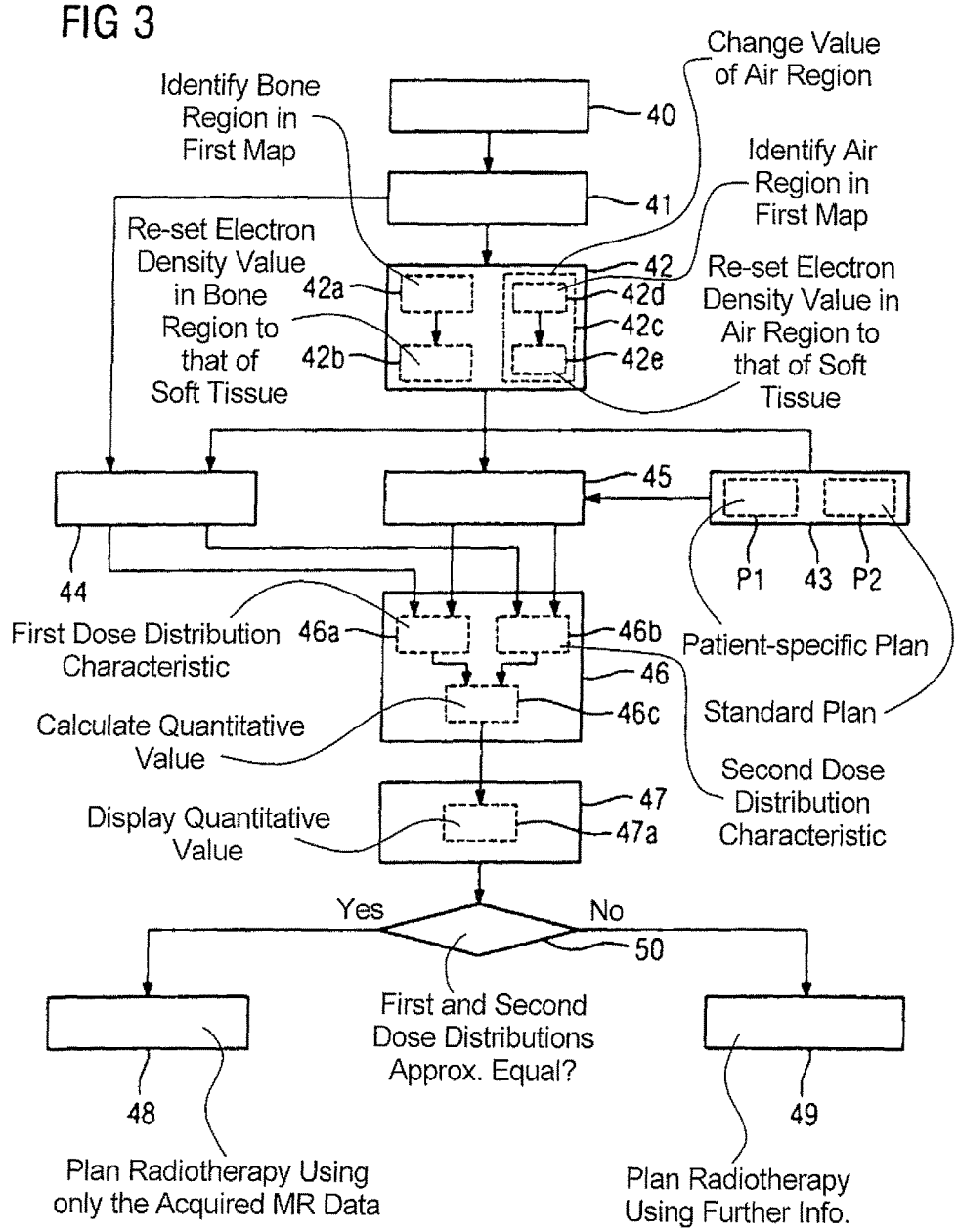

METHOD AND MAGNETIC RESONANCE APPARATUS FOR QUALITY CONTROL IN PLANNING RADIOTHERAPY OF A PATIENT

BACKGROUND OF THE INVENTION

Field of the Invention

The invention concerns a method for quality control in planning radiotherapy of a patient, as well as a radiotherapy planning computer, a magnetic resonance apparatus and a non-transitory, computer-readable data storage medium for implementing such a method.

Description of the Prior Art

With radiation therapy, target tissue, such as a tumor, of a patient is irradiated with ionizing radiation. External radiation therapy, in which radiotherapy of the body of the patient is implemented from a radiation source outside of the body, is known for use in this context. Internal radiation therapy, also called brachytherapy, is also known. With brachytherapy, radiation sources, composed of radioactive substances, are introduced into the body of the patient to locally damage or destroy target tissue in the body of the patient.

It is known to plan and/or monitor radiation therapy of a patient by the use of imaging. For this purpose a radiotherapy plan is conventionally created with the use of medical image data of the patient, which have been created using a three-dimensional imaging method. Computed tomography image data (CT image data) is conventionally used for this purpose. Using the CT image data the target volume for radiotherapy can be defined, and surrounding tissue that is to be spared—for example neuronal tissue—can be localized. Furthermore, the intensity values of the image voxels of the image data (measured in "Hounsfield Units") map the electron density at the corresponding location in the body of the patient to a good approximation, since the intensity values of the image voxels are based on absorption of the imaging X-ray radiation at the associated locations. In this way the CT image data can be converted particularly easily into an electron density map for radiotherapy planning. In the case of radiotherapy, the intensity of the interaction of the radiotherapy radiation correlates with the electron density in the body, so the attenuation of the radiation as it passes through the body can be calculated from the CT image data relatively easily. Due to this property, the preference has conventionally been to use CT image data when preparing radiotherapy planning.

There is a need, however, to use other imaging modalities in radiotherapy planning that have better soft tissue contrast in order to enable improved identification of target organs and/or at-risk organs. One imaging modality that satisfies the need for better soft tissue contrast is magnetic resonance imaging (MR imaging) by the use of a magnetic resonance apparatus (scanner). With MR imaging, the contrast depends on the distribution of the spin density of nuclear spins that have been excited, the interaction of the spins among each other and/or with their surroundings. A soft tissue contrast can be attained that is far superior to the contrast that can be attained with computed tomography.

In a magnetic resonance apparatus, also called a magnetic resonance tomography system, the body of an examination person, in particular a patient, to be examined is conventionally exposed to a relatively high basic magnetic field, for example of 1.5 or 3 or 7 tesla, produced by a basic field magnet. In addition, gradient pulses are activated by a gradient coil arrangement. Radio-frequency pulses (excitation pulses) are emitted by a radio-frequency antenna unit by suitable antenna devices, and this leads to the nuclear spins of specific atoms, excited in a resonant manner by these radio-frequency pulses, being tilted by a defined flip angle with respect to the magnetic field lines of the basic magnetic field. When the nuclear spins relax, radio-frequency signals, known as magnetic resonance signals, are emitted which are received by suitable radio-frequency antennae and then processed further. Finally, the desired image data are reconstructed from the raw data acquired in this way.

Combined use of CT imaging and magnetic resonance-imaging is known for radiotherapy planning (planning radiotherapy). The acquired CT image data and magnetic resonance image data are then typically overlaid by image registration for radiotherapy planning. The main benefit of CT image data in radiotherapy planning is to supply electron densities and geometric precision, while the magnetic resonance image data typically supplies better clinical information on target organs and/or at-risk organs.

One development in recent years under the designation of magnetic resonance-only radiotherapy planning ("MR-only RT Planning", MRORTP) envisages eliminating the CT image data from the planning process in suitable clinical applications. In this way, radiotherapy planning should occur using only magnetic resonance image data acquired from the patient. In this way, for example, a number of necessary patient scans (only magnetic resonance scans instead of both CT scans and magnetic resonance scans) can be reduced and/or possible registration errors between the CT image data and magnetic resonance image data can be avoided.

MR-only RT planning, however, poses new challenges. The electron density map required for the dosage calculation in the radiotherapy planning can be determined from magnetic resonance image data only with greater algorithmic effort than is the case for CT data. In contrast to CT image data, image contrasts in magnetic resonance image data typically do not have a clear physical relationship with the electron density and therewith photon attenuation. For example, neither bone regions nor air regions exhibit any signal in conventional magnetic resonance contrasts. This means bone regions as well as air regions are typically both black in the magnetic resonance image data, even though they have different electron densities and therefore different photon attenuations.

SUMMARY OF THE INVENTION

An object of the invention is to enable quality control of radiotherapy planning, based only on magnetic resonance image data.

The inventive method of quality control for planning radiotherapy of a patient includes the following steps.

Magnetic resonance image data of the patient are acquired from a planning volume.

A first electron density map of the planning volume is calculated in a computer using the magnetic resonance image data.

A second electron density map is calculated in a computer using the first electron density map, wherein there is a reduction in a second value of the electron density in the second electron density map compared to a first value of the electron density in the first electron density map for at least one bone region in the planning volume.

A radiotherapy plan for radiotherapy of a target volume, which is localized in the planning volume, is provided to the computer.

A first radiation dose distribution in the planning volume is calculated in the computer from the radiotherapy plan and the first electron density map.

A second radiation dose distribution in the planning volume is calculated in the computer from the radiotherapy plan and the second electron density map.

The first radiation dose distribution is composed in the computer with the second radiation dose distribution.

The computer generates output information using a result of the comparison, and making the output information available from the computer as an electronic output signal.

The generated output information can then be displayed for a user on a display monitor. Alternatively or additionally, the output information can be stored in s database. Alternatively or additionally, the output information can be transferred to a further computer system, and the further computer system can then process the output information further.

The planning volume can encompass the target volume of the radiotherapy and at least one at-risk volume for radiotherapy. The target volume and/or the at least one risk volume can be marked semi-automatically or manually in the magnetic resonance image data acquired from the planning volume and/or in the first electron density map. This can be done, for example, by marking a point or a 2D or 3D region-of-interest (ROI). The planning volume is therefore typically chosen to be large enough for the target volume and the at least one at-risk volume to be included in the planning volume. If, for example, the prostate of the patient is selected for radiotherapy, the planning volume can encompass the entire pelvic area of the patient. The target volume encompasses the target structures in the body of the patient which are to be irradiated by the radiation therapy. The target tissue is typically localized in the target volume. A radiation dose can be allocated to the target volume in radiotherapy planning. The target volume is typically delimited from the at least one at-risk volume. The at least one at-risk volume encompasses healthy tissue that is at risk of being damaged in the radiotherapy. A maximum dose, which must not be exceeded during radiation therapy, can be allocated to the at least one at-risk volume in radiotherapy planning.

An electron density map is a spatially resolved distribution of the electron density. The electron density map can be two-dimensional or three-dimensional in design. The entries in the electron density map can be in units that characterize the electron density, such as a linear attenuation coefficient with a unit of 1/m. The first electron density map, therefore, constitutes the spatially resolved distribution of the electron density in the planning volume, and this is determined on using magnetic resonance image data only. No further medical image data aside from the magnetic resonance image data are used for ascertaining the first electron density map. Ascertaining the first electron density map can be done by creating data known as "synthetic CT image data" from the magnetic resonance image data. The synthetic CT image data, which are generated, using only the magnetic resonance image data, are medical image data in the same patient geometry of the magnetic resonance image data, but with a grayscale distribution that would exist if CT image data had been acquired from the same patient. The synthetic CT image data or the first electron density map can then be used for MR-only RT planning.

Exemplary methods for ascertaining the first electron density map from the magnetic resonance image data are based, for example, on automatic, semi-automatic or manual segmenting of the magnetic resonance image data into different tissue categories, such as water, fat, air, possibly bones. It is also conceivable to use atlas-based methods for ascertaining the first electron density map from the magnetic resonance image data. A number of mutually co-registered pairs of atlas magnetic resonance image data and atlas CT image data can be present in the atlas for this purpose, and the first electron density map can be calculated from the magnetic resonance image data by consulting the atlas. It is also conceivable for the magnetic resonance image data to be acquired by a specific magnetic resonance sequence that uses ultra-short echo times, so magnetic resonance signals can be received from bones of the patient. In this way, for example, masking of the magnetic resonance image data is possible for ascertaining bone masks and/or air masks for calculating the first electron density map. Multi-contrast magnetic resonance imaging can also provide an advantageous basis for segmenting the magnetic resonance image data in order to create the first electron density map. Further possible methods for ascertaining the first electron density map from the magnetic resonance image data can be based, for example, on pattern recognition and/or image normalization and/or classification and/or bias field estimation. Methods for ascertaining the synthetic CT image data, i.e. the first electron density map, from the magnetic resonance image data are known to those skilled in the art, and thus need not be described in more detail herein.

Methods for ascertaining the first electron density map from the magnetic resonance image data have different precision and/or robustness, however, particularly in bone regions in the patient. Misallocations of bones, soft tissue or air in specific regions thus can occur with many algorithms. Problems in the correct allocation of the electron density to the magnetic resonance image data can also occur in the case of air inclusions in the patient (known as air regions or air pockets). In some cases a misallocation of bone regions and/or air regions when calculating the first electron density map can lead to only slight deviations in the calculated dose distribution compared to a dose distribution calculated using real CT image data. However, for tumors close to bones, greater errors can occur in the dose distribution if the electron density in the synthetic CT image data is incorrectly estimated in the vicinity of the tumor. It is therefore often necessary in the case of magnetic resonance-only radiation therapy to make an estimation as to whether a reliable dosage calculation can be made for radiotherapy planning on the calculated first electron density map, i.e. the synthetic CT image data, or whether recording of further planning image data, in particular recording of real CT image data, should be carried out in a specific individual case for safety, in order to rule out potential errors in MR-only RT planning.

To enable quality control of the first electron density map, in accordance with the invention the aforementioned second electron density map is calculated on the basis of the first electron density map. The second electron density map is created by executing an algorithm that has the first electron density map as an input parameter. The first electron density map may be the sole input parameter to this algorithm. The algorithm then processes the first electron density map to create the second electron density map. During this processing, a second value of the electron density is reduced in the second electron density map compared to a first value of the electron density in the first electron density map for at least one bone region in the planning volume. As described in more detail below, the value of the electron density for the at least one bone region is advantageously set to a value of an electron density of soft tissue. The second electron density map can then be regarded as a continuous soft tissue map.

A radiotherapy plan is supplied for radiotherapy of the target volume in order to determine the effect of the changes between the first electron density map and the second electron density map. The radiotherapy plan is loaded from a database and/or created by a planning program. The radiotherapy plan includes settings for a radiotherapy system, by means of which radiotherapy of the target volume can be implemented. In the case of external radiotherapy of the target volume by a linear accelerator, the radiotherapy plan can include, for example, radiotherapy angles, settings of collimators, radiotherapy energies, radiotherapy times, etc. As described in more detail below the radiotherapy plan can either be specifically matched to the radiotherapy of the patient, or can be a standard radiotherapy plan.

The first dose distribution and the second dose distribution are then calculated using the same supplied radiotherapy plan. The first dose distribution is based on the first electron density map, while the second dose distribution is based on the second electron density map. The first dose distribution can indicate a spatially resolved distribution of dose values that exists if the patient is irradiated using the radiotherapy plan and if electron density in the planning volume is formed according to the first electron density map. In this way the second dose distribution can indicate a spatially resolved distribution of dose values that exist if the patient is irradiated using the radiotherapy plan and if electron density is formed in the planning volume according to the second electron density map.

The comparison of the first dose distribution and second dose distribution can be a determination of deviations and/or matches between the first dose distribution and the second dose distribution. For example, relevant values of the two dose distributions can be compared with each other. Differences in the maximum dose value in the target volume, in the mean target volume dose or in the characteristic of the dose-volume histogram can be calculated between the two dose distributions for example, as described in more detail below. The effect of the electron density values of the at least one bone region on a dose, which is applied during radiotherapy, thus can be determined using the comparison of the first dose distribution and the second dose distribution.

The deviations and/or matches that have been ascertained in the comparison can then form part of the generated output information. The output information can be, for example, processed magnetic resonance image data, wherein a difference and/or a match between the first dose distribution and the second dose distribution is/are identified in the processed magnetic resonance image data. The output information can also be abstracted information. For example, the output information can also be numerical values that characterize an extent of a deviation and/or match between the first dose distribution and the second dose distribution.

If the deviations, which result from the comparison between the first dose distribution and the second dose distribution, are large, it can be assumed that the presence of the bones in the planning volume has a great effect on the dose applied by radiotherapy. In this case it can be expedient, for example, to manually check again the first electron density map generated on the basis of magnetic resonance image data only for whether the electron density has been correctly allocated to the bone region in the first electron density map. If the deviations that result from the comparison between the first dose distribution and the second dose distribution are fairly low, a slight effect of the presence of the bones on the dose applied by means of radiotherapy can be assumed. In this case the validity of the first electron density map created by magnetic resonance image data only can be assumed for the specific radiotherapy of the patient.

In this way the described procedure thus supplies a quality indicator for the dose-calculation that is produced on the basis of magnetic resonance image data only. The described procedure thus makes a decision easier for a user between conventional radiotherapy planning using CT image data and MR-only RT planning. The described procedure provides an indicator of the robustness of radiotherapy planning on solely synthetic CT image data. The described steps can proceed completely automatically, or semi-automatically. A subjective decision, based on qualitative experiences of radio-oncologists can be underpinned by the inventive procedure by quantitative values whose calculation requires only low user effort. Low quality radiotherapy treatments due to MR-only RT planning can be ruled out. At the same time the quality level of the radiotherapy treatments can be increased by identification of the patients suitable for magnetic resonance-based and CT-based planning.

It is particularly advantageous in this connection for the decision to be supported specifically for the individual patient, since the first and second electron density maps are created using the magnetic resonance image data specifically acquired from the patient. In certain applications the radiotherapy plan matched to the patient can also be incorporated in the described method. The decision for planning the radiotherapy is thereby supported in a respective individual case for specific patients. A user output based on the output information can be specifically linked to a patient case in this way.

In an embodiment, using the generated output information, radiotherapy is planned using only the magnetic resonance image data acquired from the planning volume. This procedure is expedient if comparison of the first dose distribution with the second dose distribution shows that there is a sufficiently small difference between the first dose distribution and the second dose distribution. For example, with a comparison as described in more detail below, of quantitative values of the first dose distribution and the second dose distribution, the quantitative deviation can be smaller than a threshold value. The output information can initiate an automatic process in this way, so planning of radiotherapy is continued on the basis of the magnetic resonance image data only. Alternatively or additionally, the output information can be displayed for a user. The user can then infer from the display that the effect of correct allocation of bone regions (and optionally air regions, see one of the paragraphs below) on the calculated dose distribution is sufficiently small in the first electron density map, in particular so small that it is tolerated within the framework of the quality system of radio oncology. Based on the output information, the user can then bring about planning of radiotherapy using only the magnetic resonance image data acquired from the planning volume.

In another embodiment, using the generated output information, further planning image data are recorded from the patient, such as using an imaging modality other than magnetic resonance imaging, wherein the further planning image data are merged into the planning of the radiotherapy of the patient. This procedure is expedient if the comparison of the first dose distribution with the second dose distribution shows that there is a greater difference between the first dose distribution and the second dose distribution. For example, with a comparison as described in more detail below, of quantitative values of the first dose distribution and the second dose distribution, the quantitative deviation can be greater than a threshold value. The output information can initiate an automatic process such that implementation of magnetic resonance-based planning of radiotherapy is stopped. Using the output information the acquisition of further planning image data therefore can be automatically arranged and/or further planning image data already acquired from the patient can be used for radiotherapy planning. Alternatively or additionally, the output information can be displayed for a user. The user can then consider the specific case of magnetic resonance-based radiotherapy planning more closely. Various courses of action are then open to the user, such as more precise analysis of the present synthetic CT image data and/or arrangement of recording of the further planning image data for the patient planning CT scan for this patient. The further planning image data is then recorded by CT imaging.

In summary, radiotherapy can be planned with the use of the generated output information using only the magnetic resonance image data acquired from the planning volume, or with the use of the generated output information further planning image data can be recorded from the patient, in particular using an imaging modality other than magnetic resonance imaging, and the further planning image data are incorporated in planning radiotherapy of the patient.

In another embodiment, calculating the second electron density map includes threshold value segmenting of the first electron density map for identifying the at least one bone region in the first electron density map. In this way the at least one bone region can be identified in the first electron density map particularly easily. This procedure is based on the consideration that bones are usually allocated much higher electron density values than other types of tissue, so the bone regions determined by threshold value segmenting during ascertainment of the first electron density map can be identified particularly easily. Of course other procedures for identifying the at least one bone region, which is to be modified when generating the second electron density map, are also conceivable. For example, when identifying the at least one bone region, information obtained when ascertaining the first electron density map can also be employed.

In another embodiment, the reduction in the second value of the electron density in the second electron density map compared to the first value of the electron density in the first electron density map is accomplished by the second value of the electron density in the at least one bone region being set to a value of an electron density of soft tissue. In particular, the electron density value can be set to the value of the electron density of soft tissue when ascertaining the second electron density map for all pixels or voxels in the at least one bone region. In this way, the at least one bone region can no longer be distinguished from the surrounding soft tissue regions in the second electron density map. The second electron density map therefore can be filled by continuous soft tissue occupancy. Examples of soft tissue are muscle tissue, water tissue, fat tissue, etc. Soft tissue typically has a lower electron density and therefore a lower absorption of photons than bone tissue. By means of the inventive procedure, the effect of the presence of the at least one bone region on radiotherapy planning can be determined particularly easily in this way when comparing the first dose distribution with the second dose distribution.

In another embodiment, calculating the second electron density map using the first electron density map is accomplished by increasing a fourth value of the electron density in the second electron density map compared to a third value of the electron density in the first electron density map for at least one air region in the planning volume. By this procedure, the effect of the at least one air region on radiotherapy planning can be analyzed in addition to the effect of the at least one bone region on radiotherapy planning. The at least one air region can be formed, for example, by air inclusions in the intestine of the patient, and these can change significantly. This described procedure is expedient if a spatial position of the at least one air region in the magnetic resonance image data or in the first electron density map is rated critical or suspect in relation to the position of the target volume and/or of the at least one risk volume.

In another embodiment, increasing the fourth value of the electron density in the second electron density map compared to the third value of the electron density in the first electron density map is accomplished by setting the fourth value of the electron density in the at least one air region to a value of an electron density of soft tissue. In this way the at least one air region in the second electron density map can be occupied analogously to the at least one bone region with the electron density of soft tissue. A particularly homogeneous second electron density map can be obtained thereby.

In another embodiment, the radiotherapy plan, which is used for ascertaining the first dose distribution of the second dose distribution, is a radiotherapy plan specifically adapted to the patient. This can be the radiotherapy plan of the patient that was created for the radiotherapy of the patient using the magnetic resonance image data. The comparison of the first dose distribution with the second dose distribution can therefore be carried out so it is well matched to the respective patient case.

In another embodiment, the radiotherapy plan, which is used for ascertaining the first dose distribution of the second dose distribution, is a standard radiotherapy plan that includes typical settings of a radiotherapy system. Such a standard radiotherapy plan can comprise typical radiotherapy settings used in a clinical application for the type of target region. Use of the standard radiotherapy plan can be sufficient in many cases for identifying the effect of the at least one bone region on an applied radiation dose even if the standard radiotherapy plan is not typically matched to the patient. Use of the standard radiotherapy plan can have the advantage that there is still no need for a radiotherapy plan individually adapted to the patient for checking the validity of the first electron density map. In this way a particularly straightforward workflow can be enabled by the use of the standard radiotherapy plan.

In another embodiment, the comparison of the first dose distribution with the second dose distribution is a comparison of at least one first dose value in the first dose distribution with at least one second dose value in the second dose distribution. The at least one first dose value can be a first maximum dose value in the target volume of the first dose distribution and the at least one second dose value can be a second maximum dose value in the target volume of the second dose distribution. The at least one first dose value can also be a first mean dose value in the target volume of the first dose distribution and the at least one second dose value can be a second mean dose value in the target volume of the second dose distribution. Further dose values are conceivable for quantitative comparison between the first dose distribution and the second dose distribution. In this way a particularly advantageous quantitative measure of a match and/or deviation between the first dose distribution and the second dose distribution can be supplied.

In another embodiment, the comparison of the first dose distribution with the second dose distribution is a comparison of a characteristic of a first dose-volume histogram of the first dose distribution with a characteristic of a second dose-volume histogram of the second dose distribution. A dose-volume histogram typically indicates which portion of the volume is irradiated with which minimum dose for the target volume and/or the at least one risk volume. A dose-volume histogram is a common instrument for objective assessment of the quality of a radiotherapy plan and for comparing radiotherapy plans. In this way, the dose-volume histogram is also suitable for comparing the first dose distribution with the second dose distribution.

In another embodiment, a quantitative value is calculated that characterizes the comparison of the first dose distribution with the second dose distribution, and the output information includes or is the quantitative value. The quantitative value can be displayed for the user on a display monitor. The user thus can be provided with a display showing the extent of the differences between the first dose distribution and the second dose distribution. The display of the quantitative value optionally can be coupled to a classification of the difference, which classification may be defined by the user. For example, slight deviations in the dose values, which lie, below a threshold value (for example 2 percent), can be marked with a first color (for example green) and large deviations in the dose value, which lie above a threshold value (for example 2 percent), can be marked with a second color (for example red). Overall, an objective indicator of the reliability of the first electron density map for the MR-only RT planning can be supplied can by this procedure.

The inventive radiotherapy planning computer has an acquisition unit, a first ascertaining unit, a calculation unit, a supply unit, a second ascertaining unit, a third ascertaining unit, a comparison unit and a generating unit individually and collectively designed for executing the inventive method.

The acquisition unit is designed to receive magnetic resonance image data of the patient acquired from a planning volume. The first ascertaining unit is designed for ascertaining a first electron density map of the planning volume using the magnetic resonance image data. The calculation unit is designed for calculating a second electron density map using the first electron density map, wherein there is a reduction in a second value of the electron density in the second electron density map compared to a first value of the electron density in the first electron density map for at least one bone region in the planning volume. The supply unit is designed for supplying a radiotherapy plan for radiotherapy of a target volume which is localized in the planning volume. The second ascertaining unit is designed for ascertaining a first dose distribution in the planning volume from the radiotherapy plan and the first electron density map. The third ascertaining unit is designed for ascertaining a second dose distribution in the planning volume from the radiotherapy plan and the second electron density map. The comparison unit is designed for comparing the first dose distribution with the second dose distribution. The generating unit is designed for generating output information using a result of the comparison and to make an electronic signal representing the output information available as an output.

The inventive magnetic resonance apparatus has an inventive radiotherapy planning computer as described above. The radiotherapy planning computer can be designed to send control signals to the magnetic resonance control computer and/or receive and/or process control signals in order to carry out the inventive method. The radiotherapy planning computer can be integrated in the magnetic resonance apparatus. The radiotherapy planning computer can also be installed separately from the magnetic resonance apparatus. The radiotherapy planning computer can be connected to the magnetic resonance apparatus. The magnetic resonance image data are acquired by a scanner of the magnetic resonance apparatus. The magnetic resonance image data can then be passed to the radiotherapy planning computer for further processing. The radiotherapy planning computer can then receive the acquired magnetic resonance image data via its acquisition unit.

The invention also encompasses a non-transitory, computer-readable data storage medium that can be loaded directly into a memory of a programmable processor of the radiotherapy planning computer. The storage medium is encoded with program code (programming instructions) that causes the inventive method to be implemented when the program code executed in the radiotherapy planning computer. The inventive method can consequently be carried out quickly, robustly and in a manner that can be identically repeated. The computer or the processor thereof must have an appropriate main memory, an appropriate graphics card or an appropriate logic unit, so the method steps can be carried out efficiently.

Examples of electronically readable data carriers are a DVD, magnetic tape or a USB stick, on which electronically readable code is stored.

The advantages of the inventive radiotherapy planning computer, the inventive magnetic resonance apparatus, and the inventive storage medium correspond to the advantages of the inventive method as described above in detail. Features, advantages or alternative embodiments mentioned in connection with the method are applicable to the other aspects of the invention. The functional features of the method are implemented by appropriate tangible modules, in particular by hardware modules.

BRIEF DESCRIPTION OF THE DRAWINGS

FIG. 1 shows an inventive magnetic resonance apparatus that includes an inventive radiotherapy planning computer.

FIG. 2 shows a first embodiment of an inventive method.

FIG. 3 shows a second embodiment of an inventive method.

DESCRIPTION OF THE PREFERRED EMBODIMENTS

FIG. 1 schematically shows an inventive magnetic resonance apparatus 11. The magnetic resonance apparatus 11 has a scanner, having a basic field magnet 17 for generating a strong and uniformly constant basic magnetic field 18. The scanner 13 has a cylindrical patient-receiving region 14 for receiving a patient 15, with the patient-receiving region 14 being cylindrically surrounded in a circumferential direction by the scanner 13. The patient 15 can be moved by a patient-positioning device 16 of the scanner 13 into the patient-receiving region 14. The patient-positioning device 16 has for this purpose an examination table arranged so as to move inside the scanner 13. The scanner 13 is shielded from the outside by m a housing shell 31.

The scanner 13 also has a gradient coil arrangement 19 for generating magnetic field gradients that are used for spatial encoding during imaging. The gradient coil arrangement 19 is controlled by a gradient control processor 28. The scanner 13 also has a radio-frequency (RF) antenna unit 20, which is designed in the illustrated example as a body coil permanently integrated in the scanner 13, and a radio-frequency antenna control processor 29. The RF control processor operates the RF antenna unit 20 to radiate RF energy that causes a magnetization of nuclear spins in the patient 15 to deviate from the polarization that is established in the basic magnetic field 18 generated by the basic field magnet 17. The radio-frequency antenna unit 20 is controlled by the radio-frequency antenna control processor 29 to irradiate radio-frequency magnetic resonance sequences into an examination space that is essentially formed by the patient-receiving region 14. The radio-frequency antenna unit 20 is also designed to receive magnetic resonance signals, in particular from the patient 15.

For controlling the basic field magnet 17, the gradient control processor 28 and the radio-frequency antenna control processor 29, the magnetic resonance apparatus 11 has a control computer 24. The control computer 24 centrally controls the magnetic resonance scanner 13, such as to carry out a predetermined imaging gradient echo sequence. Control information, such as imaging parameters, and reconstructed magnetic resonance images, can be supplied for a user on an output interface, in the present case a display monitor 25, of the magnetic resonance apparatus 11. Furthermore, the magnetic resonance apparatus 11 has an input interface 26, via which a user can enter information and/or parameters during a scanning process. The control computer 24 can include the gradient control processor 28 and/or the radio-frequency antenna control processor 29 and/or the display monitor 25 and/or the input interface 26.

The illustrated magnetic resonance apparatus 11 can have further components that magnetic resonance apparatuses conventionally have. The general mode of operation of a magnetic resonance apparatus is known to those skilled in the art, so a detailed description of the further components is not necessary herein.

The illustrated magnetic resonance apparatus 11 has a radiotherapy planning computer 27, which includes an acquisition unit 32, a first ascertaining unit 33, a calculation unit 34, a supply unit 35, a second ascertaining unit 36, a third ascertaining unit 37, a comparison unit 38 and a generating unit 39. In this way the radiotherapy planning computer 27 is designed for carrying out the method according to FIGS. 2-3.

For carrying out an inventive method alone, the radiotherapy planning computer 27 will load magnetic resonance image data from a database via the acquisition unit 32. If the inventive method is carried out by the magnetic resonance apparatus 11 and the radiotherapy planning computer 27 combined, the acquisition unit 32 of the radiotherapy planning computer 27 will receive magnetic resonance image data acquired by the scanner 13 of the magnetic resonance apparatus 11. For this purpose the acquisition unit 27 is connected to the control computer 24 of the magnetic resonance apparatus 11 for an exchange of data.

FIG. 2 shows a flowchart of a first embodiment of an inventive method of quality control for planning radiotherapy of a patient 15.

In a first method step 40 magnetic resonance image data of the patient 15 is acquired from a planning volume by means of the acquisition unit 32.

In a further method step 41 a first electron density map of the planning volume is ascertained using the magnetic resonance image data by means of the first ascertaining unit 33.

In a further method step 42 a second electron density map is calculated using the first electron density map by means of the calculation unit 34, wherein there is a reduction in a second value of the electron density in the second electron density map compared to a first value of the electron density in the first electron density map for at least one bone region in the planning volume.

In a further method step 43 a radiotherapy plan for radiotherapy of a target volume is supplied, which volume is localized in the planning volume, by means of the supply unit 35.

In a further method step 44 a first dose distribution in the planning volume is ascertained from the radiotherapy plan and the first electron density map by means of the second ascertaining unit 36.

In a further method step 45 a second dose distribution in the planning volume is ascertained from the radiotherapy plan and the second electron density map by means of the third ascertaining unit 37.

In a further method step 46 the first dose distribution is compared with the second dose distribution by means of the comparison unit 38.

In a further method step 47 output information is generated using a result of the comparison by means of the generating unit 39.

FIG. 3 shows a flowchart of a second embodiment of an inventive method of quality control for planning radiotherapy of a patient 15.

The following description is essentially limited to the differences from the exemplary embodiment in FIG. 2, with reference being made with respect to unchanging method steps to the description of the exemplary embodiment in FIG. 2. Method steps that are essentially unchanged are basically numbered with the same reference numerals.

The embodiment of the inventive method shown in FIG. 3 essentially comprises the method steps 40, 41, 42, 43, 44, 45, 46, 47 of the first embodiment of the inventive method according to FIG. 2. In addition, the embodiment of the inventive method shown in FIG. 3 has additional method steps and sub-steps. A method sequence alternative to FIG. 3 is also conceivable which has only some of the additional method steps and/or sub-steps illustrated in FIG. 3. Of course a method sequence alternative to FIG. 3 can also have additional method steps and/or sub-steps.

In the case shown in FIG. 3, calculating the second electron density map in further method step 42 is done by threshold value segmenting of the first electron density map for identifying the at least one bone region in the first electron density map in a sub-step 42a of further method step 42. In a further sub-step 42b the reduction in the second value of the electron density in the second electron density map compared to the first value of the electron density in the first electron density map can be the second value of the electron density in the at least one bone region being set at a value of an electron density of soft tissue. In this way the electron density can be set at a value of an electron density of soft tissue for calculation of the second electron density map for the at least one bone region identified in sub-step 42a.

It is also conceivable for an optional step 42c to occur during further method step 42 in which an electron density of at least one air region is changed in the second electron density map compared to the first electron density map. Calculating the second electron density map using the first electron density map then includes increasing a fourth value of the electron density in the second electron density map compared to a third value of the electron density in the first electron density map for at least one air region in the planning volume. Threshold value segmenting of the first electron density map for identifying the at least one air region in the first electron density map can in turn be carried out for this purpose in a sub-step 42d of the optional step 42c. In a sub-step 42e of optional step 42c the fourth value of the electron density in the at least one air region can then be set at a value of an electron density of soft tissue.

The radiotherapy plan, which is supplied in further method step 43, can be a radiotherapy plan P1 specifically adapted to the patient 15 or a standard radiotherapy plan P2 that includes typical settings of a radiotherapy system.

In the case shown in FIG. 3, the comparison of the first dose distribution with the second dose distribution in further method step 46 is a comparison of at least one first dose value in the first dose distribution with at least one second dose value in the second dose distribution in a sub-step 46a of further method step 46. The at least one first dose value and the at least one second dose value comprise a maximum and/or mean dose value in the target volume. Alternatively or additionally the comparison of the first dose distribution with the second dose distribution in further method step 46 can be a comparison of a characteristic of a first dose-volume histogram of the first dose distribution with a characteristic of a second dose-volume histogram of the second dose distribution in a sub-step 46b of further method step 46. In a sub-step 46c a quantitative value can then be calculated, based on a result of the comparison in sub-step 46a and/or sub-step 46b, which value characterizes the comparison of the first dose distribution with the second dose distribution. The output information can then be the quantitative value. For example, an output of the result of the comparison on the output unit can be an output of the quantitative value on the display monitor in a sub-step 47a.

The result of the comparison can be analyzed in an analysis step 50. For example, it can be determined in the analysis step how large the deviation between the first dose distribution and the second dose distribution is. The output information can be generated using this analysis. With the aid of the generated output information radiotherapy can then be planned in a further method step 48 using only the magnetic resonance image data acquired from the planning volume. This is the case, in particular, if the first dose distribution largely matches the second dose distribution. Alternatively, with the aid of the generated output information further planning image data can be recorded from the patient 15 in a further method step 49, in particular using a different imaging modality to magnetic resonance imaging, with the further planning image data being incorporated in planning the radiotherapy of the patient 15.

With the use of radiotherapy planning, which is carried out as a function of the result of the comparison, radiotherapy of the patient 15 can then be carried out by a radiation therapy computer either using only the magnetic resonance image data or consulting or using only the further planning image data.

The method steps of the inventive method illustrated in FIG. 2-3 are carried out by the radiotherapy planning computer. For this purpose the radiotherapy planning computer has the requisite software and/or computer programs that are stored in a memory of the radiotherapy planning computer. The software and/or computer programs include program code configured to carry out the inventive method when the computer program and/or the software is executed in the radiotherapy planning computer 27 or a processor of the radiotherapy planning computer 27.

Although modifications and changes may be suggested by those skilled in the art, it is the intention of the inventor to embody within the patent warranted hereon all changes and modifications as reasonably and properly come within the scope of his contribution to the art.

I claim as my invention:

1. A quality control method for planning radiotherapy of a patient, comprising:
   providing a computer with magnetic resonance image data acquired from a planning volume of a patient;
   in said computer, using the magnetic resonance data to generate a first electron density map of said planning volume, said first electron density map having a first value of the electron density for at least one bone region in the planning volume;
   in said computer, using said first electron density map to calculate a second electron density map, said second electron density map having a second value of the electron density for said at least one bone region, that is reduced with respect to said first value of said electron density for said at least one bone region;
   providing said computer with an electronic designation of a radiotherapy plan for implementing radiotherapy of a target volume situated in said planning volume;
   in said computer, using said radiotherapy plan and said first electron density map to determine a first radiation dose distribution in the planning volume;
   in said computer, using said radiotherapy plan and said second electron density map to determine a second radiation dose distribution in the planning volume;
   in said computer, comparing said first radiation dose distribution with said second radiation dose distribution to obtain a comparison result; and
   in said computer, using said comparison result to generate output information related to implementation of said radiotherapy plan, and making an electronic signal representing said output information available from said computer as an output.

2. A method as claimed in claim 1 comprising, in said computer, generating a final radiation therapy plan using only said output information and said magnetic resonance image data acquired from said planning volume.

3. A method as claimed in claim 1 comprising, dependent on said output information, acquiring further planning image data from the patient using a different imaging modality than magnetic resonance imaging, and merging said further planning image data into planning of said radiotherapy of the patient.

4. A method as claimed in claim 1 comprising calculating said second electron density map in said computer by threshold value segmenting of said first electron density map to identify said at least one bone region in said first electron density map.

5. A method as claimed in claim 1 comprising reducing said second value of said electron density in said second electron density map relative to said first value of said electron density of said at least one bone region in said first electron density map by setting said second value of the electron density in said at least one bone region to a value of electron density of soft tissue.

6. A method as claimed in claim 1 wherein said first electron density map comprises at least one air region in said planning volume that has a third electron density value, and calculating said second electron density map using said first electron density map by increasing a fourth value of electron density in said air region relative to said third value.

7. A method as claimed in claim 6 comprising increasing said fourth value of the electron density in said second electron density map relative to said third value of the electron density in said first electron density map by setting the fourth value of the electron density in said at least one air region to a value of electron density of soft tissue.

8. A method as claimed in claim 1 comprising using said output information in said computer to generate a final radiotherapy plan specifically adapted to the patient.

9. A method as claimed in claim 1 comprising providing an electronic designation of a standard radiotherapy plan to said computer, as said radiotherapy plan.

10. A method as claimed in claim 1 comprising comparing said first radiation dose distribution with said second radiation dose distribution in said computer by comparing at least one first radiation dose value in said first radiation dose distribution with at least one second radiation dose value in said second radiation dose distribution.

11. A method as claimed in claim 1 comprising comparing said first radiation dose distribution with said second radiation dose distribution in said computer by comparing a characteristic of a first radiation dose-volume histogram of said first radiation dose distribution with a characteristic of a second radiation dose-volume histogram of said second radiation dose distribution.

12. A method as claimed in claim 1 comprising from said comparison result, calculating a quantitative value in said computer that characterizes the comparison of the first radiation dose distribution with the second radiation dose distribution, and including said quantitative value in said output information.

13. A radiotherapy planning computer, comprising:
a processor having an input that receives magnetic resonance image data acquired from a planning volume of a patient;
said processor being configured to use the magnetic resonance data to generate a first electron density map of said planning volume, said first electron density map having a first value of the electron density for at least one bone region in the planning volume;
said processor being configured to use said first electron density map to calculate a second electron density map, said second electron density map having a second value of the electron density for said at least one bone region, that is reduced with respect to said first value of said electron density for said at least one bone region;
said input of said processor also receiving an electronic designation of a radiotherapy plan for implementing radiotherapy of a target volume situated in said planning volume;
said processor being configured to use said radiotherapy plan and said first electron density map to determine a first radiation dose distribution in the planning volume;
said processor being configured to use said radiotherapy plan and said second electron density map to determine a second radiation dose distribution in the planning volume;
said processor being configured to compare said first radiation dose distribution with said second radiation dose distribution to obtain a comparison result; and
said processor being configured to use said comparison result to generate output information related to implementation of said radiotherapy plan, and making an electronic signal representing said output information available from said computer as an output.

14. A magnetic resonance apparatus comprising:
a magnetic resonance data acquisition scanner;
a computer configured to operate the magnetic resonance data acquisition scanner to acquire magnetic resonance image data acquired from a planning volume of a patient;
said computer being configured to use the magnetic resonance data to generate a first electron density map of said planning volume, said first electron density map having a first value of the electron density for at least one bone region in the planning volume;
said being configured to use said first electron density map to calculate a second electron density map, said second electron density map having a second value of the electron density for said at least one bone region, that is reduced with respect to said first value of said electron density for said at least one bone region;
said computer being configured to receive with an electronic designation of a radiotherapy plan for implementing radiotherapy of a target volume situated in said planning volume;
said computer being configured to use said radiotherapy plan and said first electron density map to determine a first radiation dose distribution in the planning volume;
said computer being configured to use said radiotherapy plan and said second electron density map to determine a second radiation dose distribution in the planning volume;
said computer being configured to compare said first radiation dose distribution with said second radiation dose distribution to obtain a comparison result; and
said computer being configured to use said comparison result to generate output information related to implementation of said radiotherapy plan, and to make an electronic signal representing said output information available from said computer as an output.

15. A non-transitory, computer-readable data storage medium encoded with programming instructions, said storage medium being loaded into a process of a radiotherapy planning computer, and said programming instructions causing said processor to:
receive magnetic resonance image data acquired from a planning volume of a patient;
use the magnetic resonance data to generate a first electron density map of said planning volume, said first electron density map having a first value of the electron density for at least one bone region in the planning volume;
use said first electron density map to calculate a second electron density map, said second electron density map having a second value of the electron density for said at least one bone region, that is reduced with respect to said first value of said electron density for said at least one bone region;
receive an electronic designation of a radiotherapy plan for implementing radiotherapy of a target volume situated in said planning volume;
use said radiotherapy plan and said first electron density map to determine a first radiation dose distribution in the planning volume;
use said radiotherapy plan and said second electron density map to determine a second radiation dose distribution in the planning volume;
compare said first radiation dose distribution with said second radiation dose distribution to obtain a comparison result; and
use said comparison result to generate output information related to implementation of said radiotherapy plan, and make an electronic signal representing said output information available from said computer as an output.

* * * * *